US012622804B2

(12) United States Patent
Garriga I Rodo

(10) Patent No.: US 12,622,804 B2
(45) Date of Patent: May 12, 2026

(54) MENSTRUAL CUP WITH EASY EXTRACTION SYSTEM

(71) Applicant: ECAREYOU INNOVATION, S.L., Barcelona (ES)

(72) Inventor: Joan Garriga I Rodo, Barcelona (ES)

(73) Assignee: ECAREYOU INNOVATION, S.L., Barcelona (ES)

( * ) Notice: Subject to any disclaimer, the term of this patent is extended or adjusted under 35 U.S.C. 154(b) by 330 days.

(21) Appl. No.: 18/686,037

(22) PCT Filed: Sep. 7, 2022

(86) PCT No.: PCT/ES2022/070562
§ 371 (c)(1),
(2) Date: Feb. 23, 2024

(87) PCT Pub. No.: WO2023/037028
PCT Pub. Date: Mar. 16, 2023

(65) Prior Publication Data
US 2025/0186243 A1     Jun. 12, 2025

(30) Foreign Application Priority Data

Sep. 13, 2021    (ES) ..................................... 21382823

(51) Int. Cl.
*A61F 5/455*          (2006.01)
*A61F 5/44*           (2006.01)
(52) U.S. Cl.
CPC .......... *A61F 5/4553* (2013.01); *A61F 5/4408* (2013.01)

(58) Field of Classification Search
CPC .... A61F 5/4404; A61F 5/4405; A61F 5/4407; A61F 5/4408; A61F 5/451; A61F 5/455; A61F 5/4553; A61F 13/2045; A61F 2205/4402
See application file for complete search history.

(56) References Cited

U.S. PATENT DOCUMENTS

| | | | |
|---|---|---|---|
| 1,996,242 A | | 4/1935 | Hagedorn |
| 3,102,541 A | * | 9/1963 | Adams .................. A61F 5/4553 604/15 |
| 3,626,942 A | * | 12/1971 | Waldron ................... A61F 6/08 604/330 |
| 11,234,857 B2 | * | 2/2022 | Miller ................... A61F 5/4553 |
| 11,344,445 B2 | * | 5/2022 | Garriga I Rodo .... A61F 5/4553 |
| 2008/0077097 A1 | * | 3/2008 | Chambers ............. A61F 5/4553 604/330 |

(Continued)

FOREIGN PATENT DOCUMENTS

KR           102083436 B1      3/2020

OTHER PUBLICATIONS

Int'l Search Report for PCT/ES2022/070562, dated Dec. 12, 2022.

*Primary Examiner* — Philip R Wiest
(74) *Attorney, Agent, or Firm* — MaxGoLaw PLLC

(57) ABSTRACT
Menstrual cup with an easy extraction system that includes a longitudinal slit (4) on the external lateral side of the receptacle (2) so that, when the lower thread-like shaped extension (3) is pulled, the wall of the receptacle (2) where the slit (4) appears is deformed and generates an air channel that communicates the lower part of the cup with the upper part of the cup breaking thus the vacuum produced by the cup once it has been correctly placed, constituting the easy extraction system of the cup (1).

3 Claims, 1 Drawing Sheet

(56)  References Cited

U.S. PATENT DOCUMENTS

| 2019/0083296 A1* | 3/2019 | Miller | A61F 5/4553 |
| 2020/0046572 A1* | 2/2020 | Hwang | A61F 5/4404 |
| 2020/0214876 A1* | 7/2020 | Tsai | A61F 5/4553 |
| 2021/0069009 A1* | 3/2021 | Im | A61F 5/4553 |
| 2023/0132920 A1* | 5/2023 | Le Court | A61F 5/4553 |
| | | | 604/330 |

* cited by examiner

MENSTRUAL CUP WITH EASY EXTRACTION SYSTEM

OBJECT OF THE INVENTION

The invention, as stated in the title of this specification, refers to a menstrual cup with an easy extraction system that contributes, to the function to which it is designed, with advantages and characteristics that will be disclosed in detail thereafter, that mean an improvement to the current state-of-art.

The object of this invention refers to a menstrual cup of the type composed by a part of flexible material formed by a upper receptacle, liquid container, that, in using position is fitted to the walls of the vagina, and a lower thread-like shaped extension that serves as extraction stem to extract the cup after its use by pulling it, that has the feature that the receptacle possesses a longitudinal slit on the external lateral side so that, when the lower extension is pulled, generates an air channel that communicates the lower part of the cup with the upper part of the cup breaking thus the vacuum.

FIELD OF APPLICATION OF THE INVENTION

The field of application of this invention is within the sector of the industry engaged in manufacturing women personal hygiene products, particularly focussing in the scope of menstrual cups.

BACKGROUND OF THE INVENTION

The menstrual cups are a product that is very well known in the market, widely used because of its comfort and because, contrary to other women personal hygiene products, it is re-usable and does not generate waste.

In general, the menstrual cup is composed of a part of soft and flexible material, for example silicone, that possesses an upper receptacle or a properly said cup, with a tread-like shaped lower extension or tail that, when pulling it, facilitates the cup extraction.

The problem is that, as for the effectiveness purpose of the cup and that therefore it prevents that the menstrual flow leaks outside, in position of use it remains very fitted to the internal walls of the vagina, to be able to withdraw it, enough strength has to be exercised pulling the tail to overcome the vacuum that is formed between the cup and the vaginal cavity, which, in addition to make the extraction uncomfortable, may cause the prolapse of the cervix.

To overcome this problem and as reference to the current state-of-the art, by the document WO2019055855A1, a menstrual cup is known to be used in the vagina. The menstrual cup has a receptacle to contain liquid and has a stem device connected to the upper part of the cup and that extends through the cavity open through the cup bottom. The stem is arranged to actuate the cup side and edge to allow an easier cup insertion and extraction.

The said solution, although effective, has the drawback of complicating the cup manufacture as it requires to give it a complex internal shape to internally extend the stem up to the cup upper edge.

The objective of this invention is, therefore, to provide the market with an alternative solution where the cup construction is very much simpler but equally effective for the same aim, to provide that the air enters to eliminate the vacuum and facilitates the extraction of the device.

On the other hand, at least the applicant is not aware of the existence of any other menstrual cup that possesses the technical and structural characteristics equal or similar to that the herein claimed possesses.

EXPLANATION OF THE INVENTION

The menstrual cup with easy extraction system that the invention proposes is set up as the utmost solution to the above-mentioned objective, the characterizing details that make it possible and that distinguish it are conveniently appearing in the final claims attached to this specification.

Concretely, what the invention proposes, as it was said above, is a menstrual cup of the type that, in an already known manner, is composed of a part of flexible material formed by an upper receptacle, liquid container, that, in using position, is fitted to the internal walls of the vagina, and a lower thread-like shaped extension that serves as extraction stem to extract the cup after its use by pulling it.

And, from the said form, the cup is distinguished by the fact it possesses an easy extraction system when breaking the vacuum generated by the cup once it was correctly placed.

More concretely, the said system consists in the existence of a longitudinal slit on the external lateral part of the receptacle that, when the lower thread-like shaped extension is pulled, the wall of the receptacle where the slit appears is deformed by the upper part and generates an air channel that communicates the lower part of the cup with the upper part of the cup breaking thus the vacuum.

DESCRIPTION OF THE DRAWINGS

To complement the description carried out and in order to assist to best understand the characteristics of the invention, attached to this specification, as an integral part thereof, a sheet of drawings is attached in which, for illustration and no limitation purpose, the following has been represented:

The FIG. 1—It shows a front elevation view of an example of embodiment of the menstrual cup with an easy extraction system object of the invention, and the external set up thereof can be seen, namely the longitudinal slit.

Figure 1:
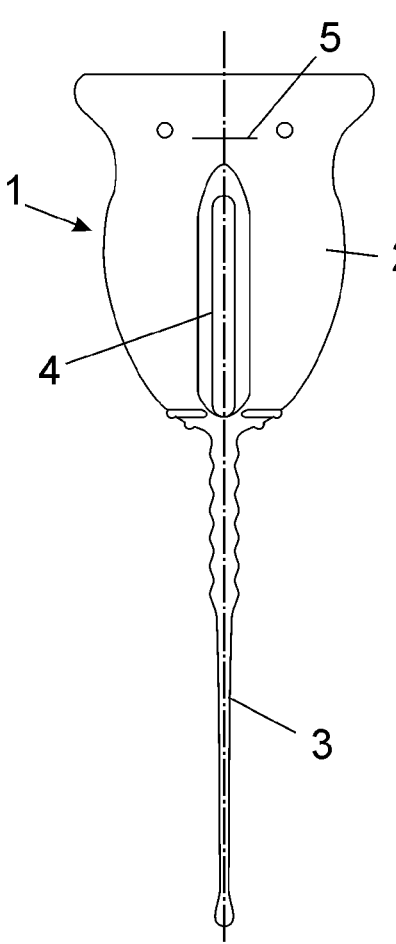
Figure 2:
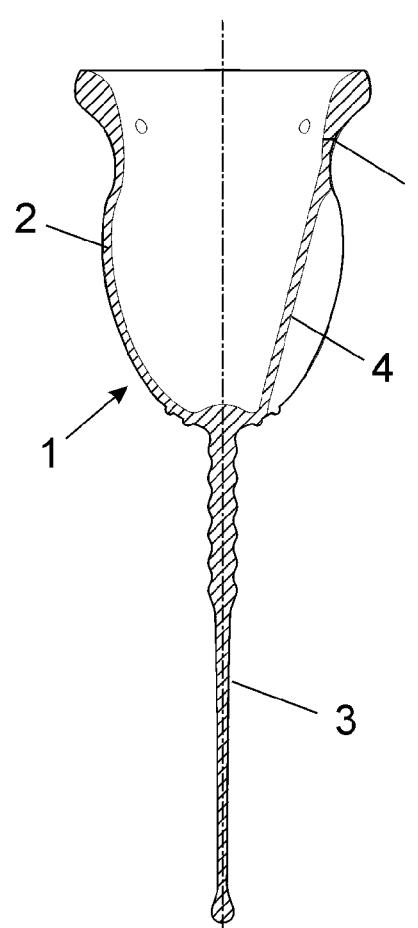
Figure 3:
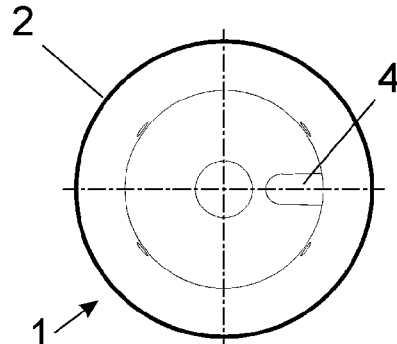

The FIG. 2—It shows a sectional view of the example of the menstrual cup of the invention, appearing in the FIG. 1, according to the section A-A stated in the said figure, the internal arrangement thereof can be seen and, namely that of the slit; and The FIG. 3—It shows an upper plan view of the cup, according to the invention, appearing in the FIGS. 1 and 2.

PREFERRED EMBODIMENT OF THE INVENTION

Seen the figures disclosed, and according to the numerals adopted in them, a no limiting example of the menstrual cup of the invention can be seen, which comprises what is disclosed in detail below.

Thus, as it can be seen in the said figures, the cup (1) is composed by a part of flexible material comprising an upper receptacle (2), liquid container, that, in using position, is fitted to the internal walls of the vagina, and a lower thread-like shaped extension (3) that serves as extraction stem to extract the cup by pulling it.

And, from the said already known arrangement, the cup (1) is distinguished in that it possesses a longitudinal slit (4) on the external lateral side of the receptacle (2) so that, when the lower thread-like extension (3) is pulled, the receptable wall (2) where the slit (4) stands is deformed and generates an air channel that communicates the lower part of the cup with the upper part of the cup breaking thus the vacuum produced by the cup when it is correctly placed, constituting a cup easy extraction system (1)

In this manner of embodiment, the said air channel is generated by the deformation first of the upper edge (2a) of the receptacle located above the slit. Thanks to the geometry of the slit, the user when pulling the lower thread-like shaped extension (3), first pulls the part of the upper edge (2a) of the receptacle that is located above the slit, provoking that this later is deformed and allows the air to pass between the lower and the upper parts of the cup. For example, the wall of the receptacle (2), where the slit (4) is located, is at least partly straight a fact that makes it shorter than the rest of the wall of the receptacle (2) that is oval-shaped.

And, in a preferred embodiment, the said air channel passes through a hole (5) located above the slit (4) so that the deformation of the upper edge (2a) of the receptacle is not necessary. In this case, the air coming from the lower part of the cup passes through the slit and enters in the upper part of the cup through the hole (5).

In an even more preferred embodiment, the hole (5) is a horizontal groove that opens when tension is applied on the lower part of the cup.

In a preferred embodiment, the lower thread-like shaped extension (3) that serves as extracting stem for, when pulling it, withdrawing the cup, is sufficiently long in order that its lower end remains outside the body of the user when the cup is correctly placed. In this preferred embodiment, the user should not introduce the fingers within the vagina but it will suffice to pull the thread-like shaped extension (3).

Sufficiently disclosed the nature of this invention, as well as the manner of implementing it, it is not deemed necessary to extend anymore its explanation in order that any man skilled in the art understands its scope and the advantages arising from it.

The invention claimed is:

1. Menstrual cup (1) with an easy extraction system that, being composed of a part of flexible material that comprises an upper receptacle (2), liquid container, that is configured to be fitted to the internal walls of the vagina, and a lower thread-like shaped extension (3) that serves as an extraction stem in order to, when pulling the extension, extract the cup (1), comprising a longitudinal slit (4) on an external lateral wall of the receptacle (2), characterized in that a wall of the receptacle (2) where the longitudinal slit (4) is located is at least partially straight while the rest of the wall of the receptable (2) is oval-shaped so that, when the lower thread-like shaped extension (3) is pulled, the wall of the receptacle (2) where the slit (4) is located is deformed and generates an air channel that communicates a lower part of the cup (1) with an upper part of the cup (1) thus breaking a vacuum produced by the cup (1) when it is correctly placed, constituting the system of easy extraction of the cup (1).

2. Menstrual cup with easy extraction system, according to the claim 1, characterized in that, on the wall of the receptacle (2), above the slit (4), a hole (5) has been provided through which the air passes between the lower part of the cup and the upper part of the cup.

3. Menstrual cup with an easy extraction system, according to claim 2, characterized in that the hole (5) is a horizontal groove.

* * * * *